United States Patent
Fabian et al.

(10) Patent No.: US 9,247,584 B2
(45) Date of Patent: Jan. 26, 2016

(54) HEAT-GENERATING APPARATUS AND METHOD OF GENERATING SMOKE

(71) Applicant: UL LLC, Northbrook, IL (US)

(72) Inventors: Zoltan Thomas Fabian, San Diego, CA (US); David Gerard Dubiel, Kansasville, WI (US); David Eugene Mills, Northbrook, IL (US)

(73) Assignee: UL LLC

( * ) Notice: Subject to any disclaimer, the term of this patent is extended or adjusted under 35 U.S.C. 154(b) by 435 days.

(21) Appl. No.: 13/837,260

(22) Filed: Mar. 15, 2013

(65) Prior Publication Data

US 2014/0260512 A1   Sep. 18, 2014

(51) Int. Cl.
*H05B 3/20* (2006.01)
*H05B 3/00* (2006.01)
*G08B 29/14* (2006.01)
*G01N 33/00* (2006.01)
(Continued)

(52) U.S. Cl.
CPC .......... *H05B 3/0038* (2013.01); *G01N 33/0006* (2013.01); *G08B 29/145* (2013.01); *F24H 3/0411* (2013.01); *F26B 3/30* (2013.01)

(58) Field of Classification Search
CPC . G01N 33/0006; H05B 3/0038; G08B 29/145
USPC ......... 392/347, 348, 349, 350, 351, 352, 353, 392/360, 365, 373, 374, 375, 376, 407, 411, 392/412, 413, 414, 415, 386, 390; 319/536, 319/537, 538, 539, 540; 43/127, 128, 129, 43/130, 131, 132.1, 133, 134, 135, 136, 43/137, 138, 139, 140, 141, 142, 143, 144
See application file for complete search history.

(56) References Cited

U.S. PATENT DOCUMENTS

| | | | | |
|---|---|---|---|---|
| 3,502,846 A | * | 3/1970 | Porwancher | A23B 4/0523 126/59.5 |
| 4,049,948 A | * | 9/1977 | Gilreath | H05B 3/06 211/100 |
| 4,093,867 A | | 6/1978 | Shah et al. | |

(Continued)

FOREIGN PATENT DOCUMENTS

| EP | 1325299 A2 | 7/2003 |
|---|---|---|
| WO | WO-0227293 A2 | 4/2002 |

OTHER PUBLICATIONS

European Written Opinion and Search Report for application No. EP 14 15 9936, dated Dec. 2, 2015.

*Primary Examiner* — John Fitzgerald
*Assistant Examiner* — Truong Phan
(74) *Attorney, Agent, or Firm* — Marshall, Gerstein & Borun LLP

(57) ABSTRACT

A heat-generating apparatus includes a frame assembly and a securement assembly carried by the frame assembly. The securement assembly includes a panel member arranged in a first vertical plane for supporting a target material parallel to the first vertical plane. The heat-generating apparatus also includes a heating support assembly adjustably supported by the frame and including at least one heating element arranged in a second vertical plane that is parallel to and offset from the first vertical plane. The heating support assembly is adjustable along a horizontal first adjustment axis that is perpendicular to each of the first and second vertical planes and along a second adjustment axis that is disposed in or adjacent to the second vertical plane.

44 Claims, 7 Drawing Sheets

(51) Int. Cl.
*F26B 3/30* (2006.01)
*F24H 3/04* (2006.01)

(56) References Cited

U.S. PATENT DOCUMENTS

| | | | |
|---|---|---|---|
| 4,629,850 A * | 12/1986 | Tanabe | H05B 6/6411 219/404 |
| 4,980,571 A | 12/1990 | McRae et al. | |
| 5,485,780 A * | 1/1996 | Koether et al. | 99/419 |
| 5,590,238 A * | 12/1996 | Ericson | B44D 3/166 134/38 |
| 5,644,071 A | 7/1997 | Wagner | |
| 5,938,959 A * | 8/1999 | Wang | 219/401 |
| 6,198,399 B1 * | 3/2001 | Mattis | 340/628 |
| 6,341,554 B2 * | 1/2002 | Thiriat | 99/327 |
| 6,543,337 B1 * | 4/2003 | Brown | 99/327 |
| 2004/0056765 A1 * | 3/2004 | Anderson et al. | 340/522 |
| 2005/0204799 A1 | 9/2005 | Koch | |
| 2005/0204927 A1 * | 9/2005 | Boyle et al. | 99/389 |
| 2005/0262924 A1 | 12/2005 | Wood et al. | |
| 2006/0261967 A1 * | 11/2006 | Marman | G08B 29/26 340/630 |

* cited by examiner

HEAT-GENERATING APPARATUS AND METHOD OF GENERATING SMOKE

FIELD OF THE DISCLOSURE

This disclosure relates generally to a testing apparatus and, more particularly, to an apparatus adapted to generate smoke by smoldering a material, for example.

BACKGROUND

In the performance testing of smoke detectors or other devices, it is necessary to repeatably generate a consistent amount of smoke and solid particulate resulting from the smoldering of a target material, such as a foam or wood material. In the past, open sources of heat, such as cigarettes or heat wires, were used to initiate smoldering of the target material. However, the open source typically generated inconsistent amounts of smoke and solid particulate, which made repeatable testing difficult. In response, radiant heat sources were employed to initiate smoldering in target materials. One or more radiant heat sources were typically positioned offset from and directly above a target material to provide some consistent amount of heat to the target material, and more consistency in smoke and particle generation was achieved. However, because the radiant heat sources were positioned directly over the area to be heated, the resulting rising smoke and particles contacted the radiant heat sources. Such contact resulted in inconsistency in the generated heat, failure of the radiant heat sources, and even fires caused by the igniting of the particulate.

To prevent contact with the smoke and particulate, the radiant heat sources were positioned to be remote from the generated smoke and particulate. For example, four radiant heat sources were positioned at right angles to form a square shape that formed a perimeter around the target material. The resulting smoke and particulate would rise in the space between the radiant heat sources, thereby eliminating the problems associated with direct contact. The radiant heat sources were fixed to a structure that supported them in the square-shaped configuration, and adjusting the position of the radiant heat sources to adjust heat intensity was difficult or impossible. Moreover, the square-shape provided non-uniform heating in the target material, resulting in inconsistent smoke generation.

BRIEF SUMMARY OF THE DISCLOSURE

An embodiment of a heat-generating apparatus includes a frame assembly and a securement assembly carried by the frame assembly. The securement assembly includes a panel member arranged in a first plane for supporting a target material. The heat-generating apparatus also includes a heating support assembly adjustably supported by the frame and including at least one heating element arranged in a second plane that is offset from the first plane. The heating support assembly is adjustable along a first adjustment axis that is perpendicular to each of the first and second planes and along a second adjustment axis that is disposed in or adjacent to the second plane. So configured, the heat-generating apparatus provides allows the heating support assembly to be quickly and easily positioned to a desired location to allow the at least one heating element to generate a suitable amount of smoke when acting upon the target material.

A method of generating smoke includes positioning a target material in a vertical orientation on a securement assembly of a heat-generating apparatus. The method further includes adjusting a vertical and/or horizontal position of a heating support assembly carried by a frame of the heat-generating apparatus relative to the target material. The heating support assembly includes at least one heating element spaced from the target material. The method also includes activating the at least one heating element to apply heat to the target material to generate smoke.

DETAILED DESCRIPTION

Figure 1:
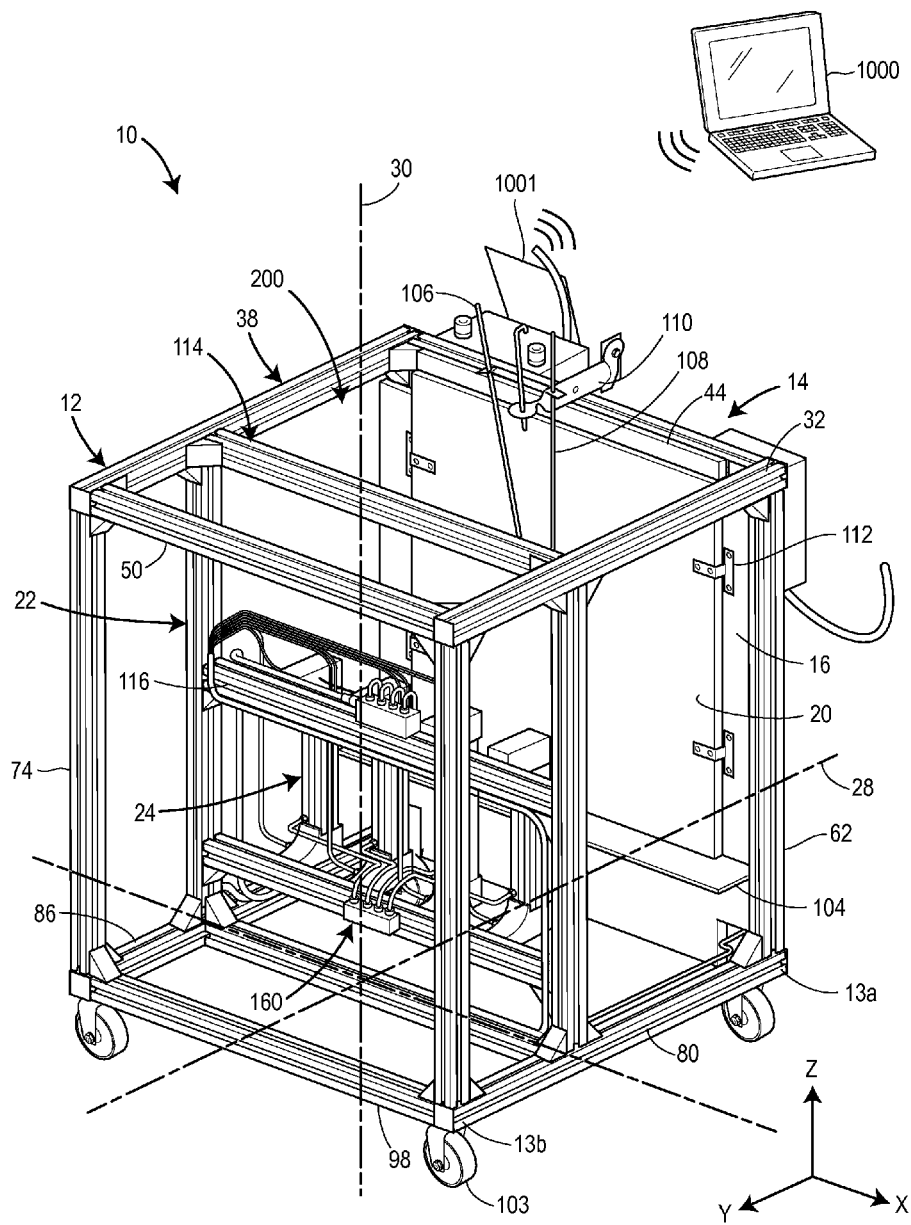
FIG. 1 is a first perspective view of an embodiment of a heat-generating apparatus.
Figure 4:
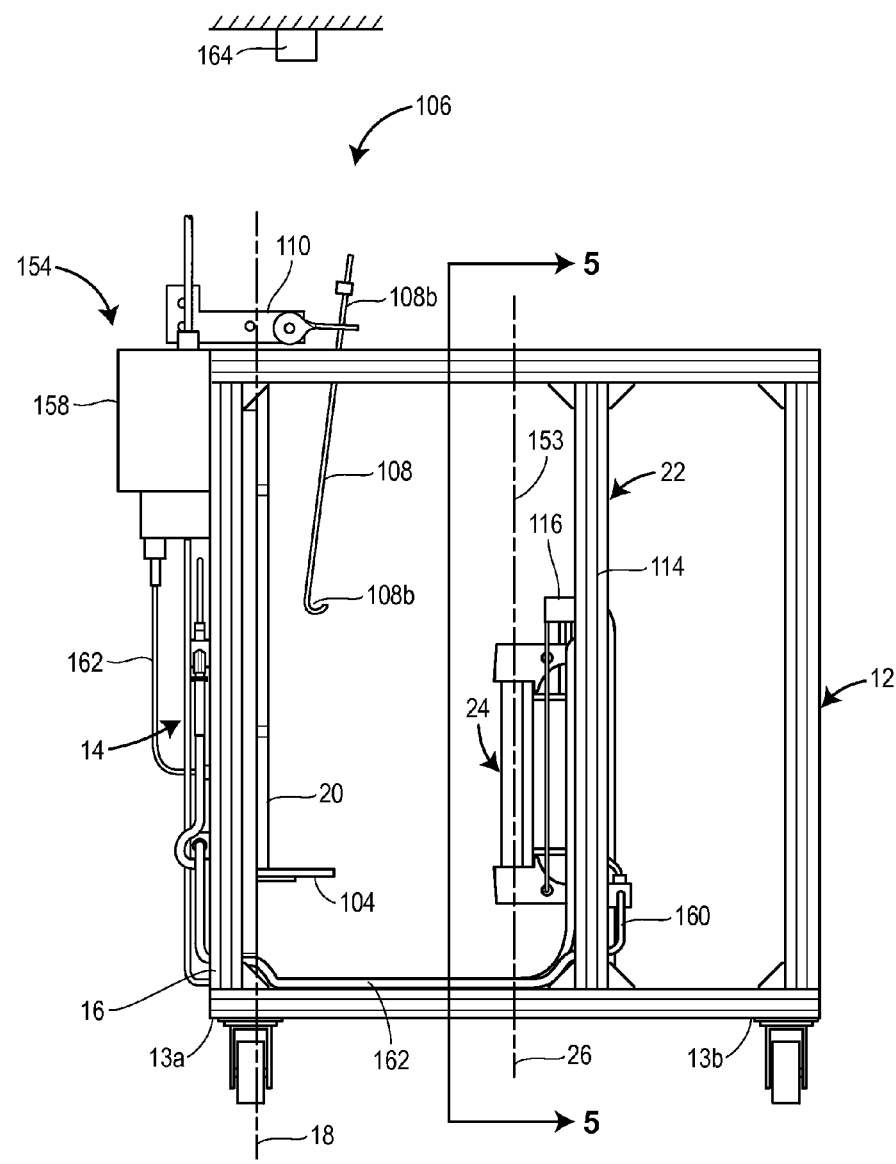
FIG. 4 is a side view of the embodiment of FIG. 1.
Figure 5:
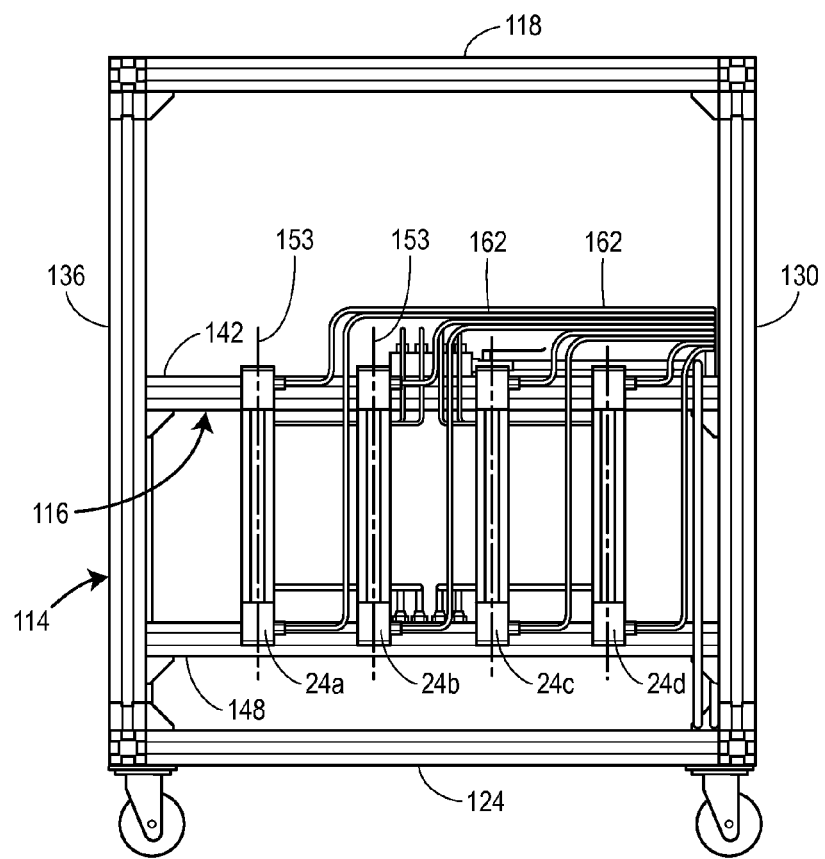
FIG. 5 is a cross-sectional view of the embodiment of FIG. 1 taken along line 5-5 of FIG. 4.

As illustrated in FIGS. 1 and 4, a heat-generating apparatus 10 constructed in accordance with the principles of the present disclosure includes a frame assembly 12 and a securement assembly 14 secured to the frame assembly 12. The securement assembly 14 includes a panel member 16 arranged in a first plane 18 (see FIG. 4) for supporting a target material 20. The first plane 18 may be vertical or substantially vertical and the target material 20 may be supported within or parallel to the vertical first plane 18. The heat-generating apparatus 10 also includes a heating support assembly 22 adjustably supported by the frame assembly 12 and including at least one heating element 24 arranged in a second plane 26 (see FIG. 4) that is offset from the first plane 18. The second plane 26 may be vertical and may be parallel to the first plane 18. The heating support assembly 22 is adjustable along a first adjustment axis 28 (see FIG. 1) that may extend in a horizontal direction. The first adjustment axis 28 may intersect, and may be perpendicular to, each of the first and second planes 18, 26. The heating support assembly 22 is also adjustable along a second adjustment axis 30 that is disposed parallel to, in, or adjacent to the second plane 26. So configured, the heat-generating apparatus 10 allows the heating support assembly 22 to be quickly and easily positioned to a desired location to allow the at least one heating element 24 to consistently and repeatably generate a desired amount of heat to generate a desired amount of smoke and solid particulate when acting on the target material 20. In addition, the vertically-aligned heating support assembly 22 may be horizontally offset from the target material 20 along the first adjustment axis 28 to avoid potentially damaging contact between the generated smoke/particulate and the at least one heating element 24.

Figure 2:
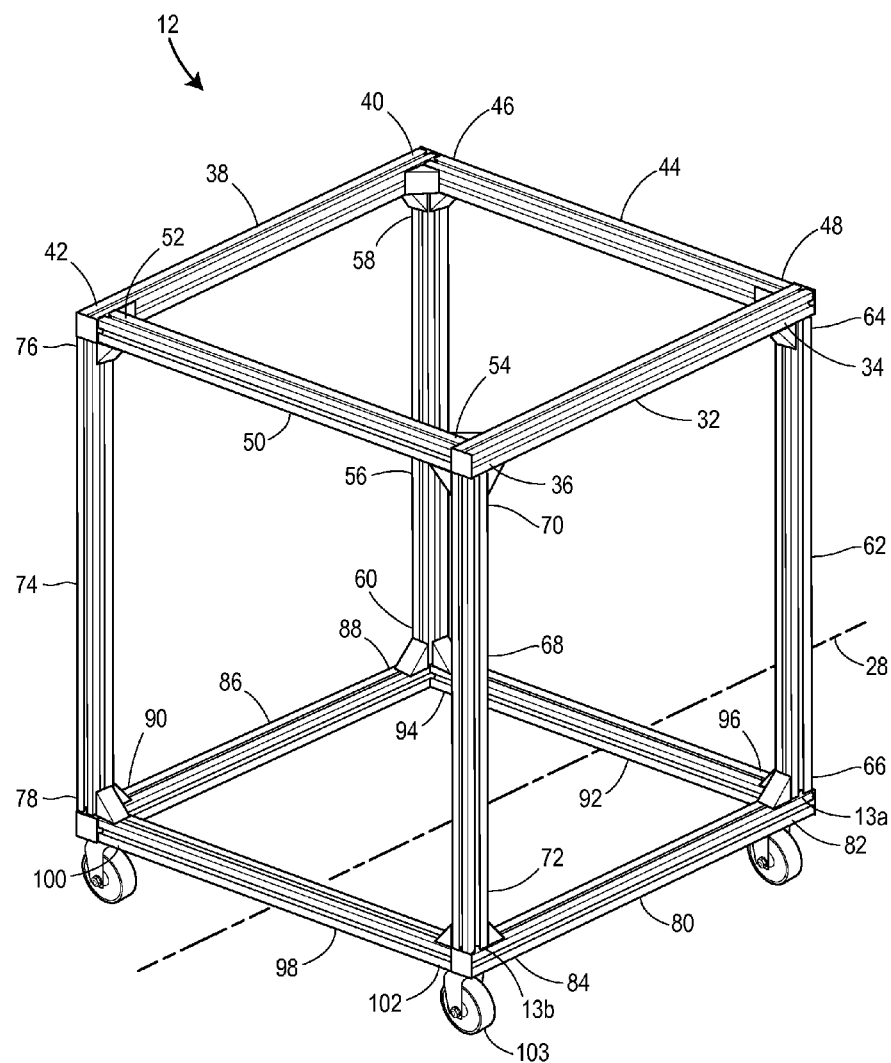
FIG. 2 is a perspective view of the frame assembly of the embodiment of FIG. 1.

Turning to the heat-generating apparatus 10 in more detail, FIGS. 1 and 2 illustrate an embodiment of the frame assembly 12. The frame assembly 12 may include any number of frame elements and may have any suitable shape or combination of shapes. For example, as illustrated in FIG. 2, the frame assembly 12 may include a first upper frame member 32 that may be elongated and may have a longitudinal axis that extends in a first horizontal direction. As used herein, a horizontal direction is a direction along a plane parallel to or coplanar with the X-Y plane of the reference coordinate system provided in FIG. 1. More specifically, the longitudinal axis of the first upper frame member 32 may extend in a first horizontal direction that is parallel to or coaxial with the Y-axis of the reference coordinate system provided in FIG. 1. The first upper frame member 32 may have a first end 34 and a second end 36 that is longitudinally-opposite to the first end 34.

Still referring to FIG. 2, the frame assembly 12 may also include a second upper frame member 38. The second upper frame member 38 may be elongated and may have a longitudinal axis that extends in the first horizontal direction, and the longitudinal axis of the second upper frame member 38 may be parallel to the longitudinal axis of the first upper frame member 32. The second upper frame member 38 may have a first end 40 and a second end 42 that is longitudinally-opposite to the first end 40, and the first end 40 may be aligned with the first end 34 of the first upper frame member 32 when viewed in a direction parallel to the X-axis of the reference coordinate system provided in FIG. 1. So configured, each of the first upper frame member 32 and the second upper frame member 38 may extends parallel to and horizontally offset from the first adjustment axis 28.

The frame assembly 12 may also include a third upper frame member 44. The third upper frame member 44 may be elongated and may have a longitudinal axis that extends in a second horizontal direction. More specifically, the longitudinal axis of the second upper frame member 38 may be parallel to or coaxial with the X-axis of the reference coordinate system provided in FIG. 1. The second upper frame member 38 may have a first end 46 and a second end 48 that is longitudinally-opposite to the first end 46. The first end 46 of the third upper frame member 44 may be secured to the first end 40 of the second upper frame member 38 and the second end 48 of the third upper frame member 44 may be secured to the first end 34 of the first upper frame member 32.

Referring again to FIG. 2, the frame assembly 12 may further include a fourth upper frame member 50, and the fourth upper frame member 50 may be elongated and may have a longitudinal axis that extends in the second horizontal direction. More specifically, the longitudinal axis of the fourth upper frame member 50 may be parallel to the longitudinal axis of the third upper frame member 44. The fourth upper frame member 50 may have a first end 52 and a second end 54 that is longitudinally-opposite to the first end 46, and the first end 52 may be aligned with the first end 46 of the third upper frame member 44 when viewed in a direction parallel to the Y-axis of the reference coordinate system provided in FIG. 1. The first end 52 of the fourth upper frame member 50 may be secured to the second end 42 of the second upper frame member 38 and the second end 54 of the fourth upper frame member 50 may be secured to the first end 36 of the first upper frame member 32.

The frame assembly 12 may further include a first intermediate frame member 56 that may be elongated and may have a longitudinal axis that extends in a vertical direction. As used herein, a vertical direction is a direction along an axis parallel to or coaxial with the Z-axis of the reference coordinate system provided in FIG. 1. The first intermediate frame member 56 may have a first end 58 and a second end 60 that is longitudinally-opposite to the first end 58. The first end 58 of the first intermediate frame member 56 may be secured to the first end 40 of the second upper frame member 38 and the second end 60 of the first intermediate frame member 56 may be secured to the first end 46 of the third upper frame member 44.

The frame assembly 12 may also include a second intermediate frame member 62 that may be elongated and may have a longitudinal axis that extends in a vertical direction. The second intermediate frame member 62 may have a first end 64 and a second end 66 that is longitudinally-opposite to the first end 64. The first end 64 of the second intermediate frame member 62 may be secured to the first end 34 of the first upper frame member 32 and the second end 66 of the second intermediate frame member 62 may be secured to the second end 48 of the third upper frame member 44.

The frame assembly 12 may also include a third intermediate frame member 68 that may be elongated and may have a longitudinal axis that extends in a vertical direction. The third intermediate frame member 68 may have a first end 70 and a second end 72 that is longitudinally-opposite to the first end 70. The first end 70 of the third intermediate frame member 68 may be secured to the second end 36 of the first upper frame member 32 and the second end 72 of the third intermediate frame member 68 may be secured to the second end 54 of the fourth upper frame member 50.

The frame assembly 12 may additionally include a fourth intermediate frame member 74 that may be elongated and may have a longitudinal axis that extends in a vertical direction. The fourth intermediate frame member 74 may have a first end 76 and a second end 78 that is longitudinally-opposite to the first end 76. The first end 76 of the fourth intermediate frame member 74 may be secured to the second end 42 of the second upper frame member 38 and the second end 78 of the fourth intermediate frame member 74 may be secured to the first end 52 of the fourth upper frame member 50.

Still referring to FIG. 2, the frame assembly 12 may include a first lower frame member 80 that may be elongated and may have a longitudinal axis that extends in the first horizontal direction. More specifically, the longitudinal axis of the first lower frame member 80 may be parallel to and vertically offset from the longitudinal axis of the first upper frame member 32. The first lower frame member 80 may have a first end 82 and a second end 84 that is longitudinally-opposite to the first end 82.

The frame assembly 12 may include a second lower frame member 86 that may be elongated and may have a longitudinal axis that extends in the first horizontal direction. More specifically, the longitudinal axis of the second lower frame member 86 may be parallel to and vertically offset from the longitudinal axis of the second upper frame member 38. The second lower frame member 86 may have a first end 88 and a second end 90 that is longitudinally-opposite to the first end 88, and the first end 88 may be aligned with the first end 82 of the first lower frame member 80 when viewed in a direction parallel to the X-axis of the reference coordinate system provided in FIG. 1.

The frame assembly 12 may include a third lower frame member 92 that may be elongated and may have a longitudinal axis that extends in the second horizontal direction. More specifically, the longitudinal axis of the third lower frame member 92 may be parallel to and vertically offset from the longitudinal axis of the third upper frame member 44. The third lower frame member 92 may have a first end 94 and a second end 96 that is longitudinally-opposite to the first end 94. The first end 94 of the third lower frame member 92 may be secured to the second end 60 of the first intermediate frame member 56 and the first end 88 of the second lower frame member 86. In addition, the second end 96 of the third lower frame member 92 may be secured to the second end 66 of the second intermediate frame member 62 and the first end 82 of the first lower frame member 80.

The frame assembly 12 may include a fourth lower frame member 98 that may be elongated and may have a longitudinal axis that extends in the second horizontal direction. More specifically, the longitudinal axis of the fourth lower frame member 98 may be parallel to and vertically offset from the longitudinal axis of the fourth upper frame member 50. The fourth lower frame member 98 may have a first end 100 and a second end 102 that is longitudinally-opposite to the first end 100, and the first end 100 may be aligned with the first end 94 of the third lower frame member 92 when viewed in a direction parallel to the Y-axis of the reference coordinate system provided in FIG. 1. The first end 100 of the fourth lower frame member 98 may be secured to the second end 78 of the fourth intermediate frame member 78 and the second end 90 of the second lower frame member 86. In addition, the second end 102 of the fourth lower frame member 98 may be secured to the second end 72 of the third intermediate frame member 68 and/or the second end 84 of the first lower frame member 80.

The frame members 32, 38, 44, 50, 56, 62, 68, 74, 80, 86, 92, 98 may have any suitable length. For example, the first, second, third, and fourth upper frame members 32, 38, 44, 50 may each have an identical length, such as such as 30 inches, for example. In addition, the first, second, third, and fourth lower frame members 80, 86, 92, 98 may each have the same length as the first, second, third, and fourth upper frame members 32, 38, 44, 50. The first, second, third, and fourth intermediate frame members 56, 62, 68, 74 may each be longer than the first, second, third, and fourth upper frame members 32, 38, 44, 50, and the first, second, third, and fourth intermediate frame members 56, 62, 68, 74 may each be 36 inches, for example. The disclosed frame members may have any suitable shape. For example, each frame member 32, 38, 44, 50, 56, 62, 68, 74, 80, 86, 92, 98 may include a tube having four longitudinal walls that are arranged to have a rectangular or square cross-sectional shape, and the four longitudinal walls may cooperate to define a hollow interior to reduce the weight of the frame members. The cross-sectional shape may be uniform along the entire longitudinal axis, or the cross-sectional shape may vary. A plurality of longitudinal ridges may be disposed on one of more of the four longitudinal walls to stiffen the frame members. The frame members may be made from any suitable material, such as a non-combustible material (e.g., aluminum or plastic). The frame assembly 12 may also include a plurality of casters 103 that allow a user to easily move the heat-generating apparatus 10 to a desired location.

Figure 6:
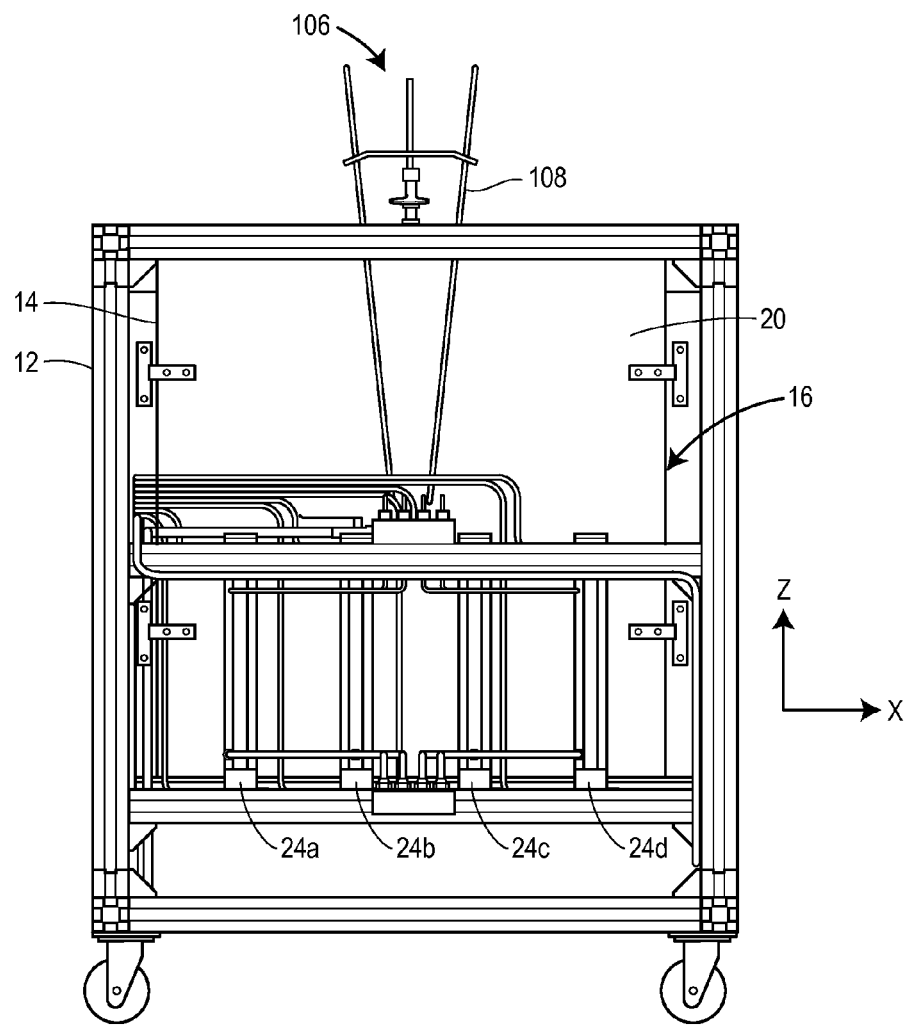
FIG. 6 is a front view of the embodiment of FIG. 1.

Referring to FIGS. 1, 4, and 6, the securement assembly 14 is attached to the frame assembly 12 and includes a panel member 16. The panel member 16 may have any suitable size and shape to allow the panel member 16 to support the target material 20. For example, the panel member 16 may be planar and may have a shape and size adapted to be attached to one or more of the third upper frame member 44, the first intermediate frame member 56, the second intermediate frame member 62, and the third lower frame member 92. The panel member 16 may be secured to one or more of the third upper frame member 44, the first intermediate frame member 56, the second intermediate frame member 62, and the third lower frame member 92 in any manner known in the art such as by clips secured to the frame members, by mechanical fasteners, or by an adhesive. The panel member 16 may be made from any suitable material. Preferably, the panel member 16 may comprise a non-combustible material, such as metal or plastic. A surface of the panel member 16 (e.g., a front surface) may be disposed in the first plane 18 (i.e., a plane coplanar with or parallel to the X-Z plane of the reference coordinate system provided in FIG. 1). Alternatively, the surface of the panel member 16 may be disposed at an angle relative to the first plane 18. The first plane 18 may be disposed at a longitudinal first end portion 13a of the frame assembly 12. That is, the first plane 18 may extend through or adjacent to the first end 34 of the first upper frame member 32 and the first end 40 of the second upper frame member 38 when viewed along an axis that may be parallel to or coaxial with the X-axis of the reference coordinate system provided in FIG. 1.

As illustrated in FIGS. 1 and 4, the securement assembly 14 may also include a support member 104 secured to the panel member 16, and the support member 104 may be planar and may extend in a horizontal or generally horizontal direction, generally perpendicular to the first plane 18. The support member 104 may be secured to one or more portions of the panel member 16. The support member 104 may also be secured to the second intermediate frame member 54 and/or the first intermediate frame member 62. The support member 104 may be positioned to support the lower end of the target material 20.

Still referring to FIGS. 1 and 4, the securement assembly 14 may optionally include an arm assembly 106, and the arm assembly 106 may include an engagement member 108 that extends in a generally vertical direction. The engagement member 108 may be pivotably coupled to a bracket 110 that may be secured to the third upper frame member 44. A spring (not shown), such as a torsional spring or a linear spring, may engage the bracket 110 and/or an upper portion 108b of the engagement member 108 to pivotally bias a lower portion 108a of the engagement member 108 towards the panel member 16 about a rotational axis that is parallel to the X-axis. So configured, the lower portion 108a of the engagement member 108 may contact the target material 20 to maintain the target material 20 in a desired upright, vertical position on the support member 104 and against the panel member 16. In addition, one or more mounting clips 112 may be secured to the panel member 16 to engage a portion of the target material 20 adjacent to a vertical side edge thereof to further secure the target material 20 to the panel member 16.

As illustrated in FIGS. 1, 4, 5, and 7, the heat-generating apparatus 10 also includes the heating support assembly 22 that is adjustable along the first adjustment axis 28 that may be horizontal and may be perpendicular to each or one of the first and second planes 18, 26. More specifically, the heating support assembly 22 may translate along an axis that may be parallel to or coaxial with the Y-axis of the reference coordinate system provided in FIG. 1. The heating support assembly 22 may translate along the first adjustment axis 28 from a first position at or adjacent to the longitudinal first end portion 13a of the frame assembly 12 to a second position at or adjacent to a longitudinal second end portion 13b of the frame assembly 12. The heating support assembly 22 may include a primary assembly 114 and a secondary assembly 116 that is carried by the primary assembly 114. The at least one heating element 24 may be secured to the secondary assembly 116, and the secondary assembly 116 may translate relative to the primary assembly 114 to displace the secondary assembly 116 along the second adjustment axis 30 parallel to or along the second plane 26 (e.g., along the Z-axis or the X-axis, or diagonally within the X-Z plane of the reference coordinate system provided in FIG. 1).

Figure 7:
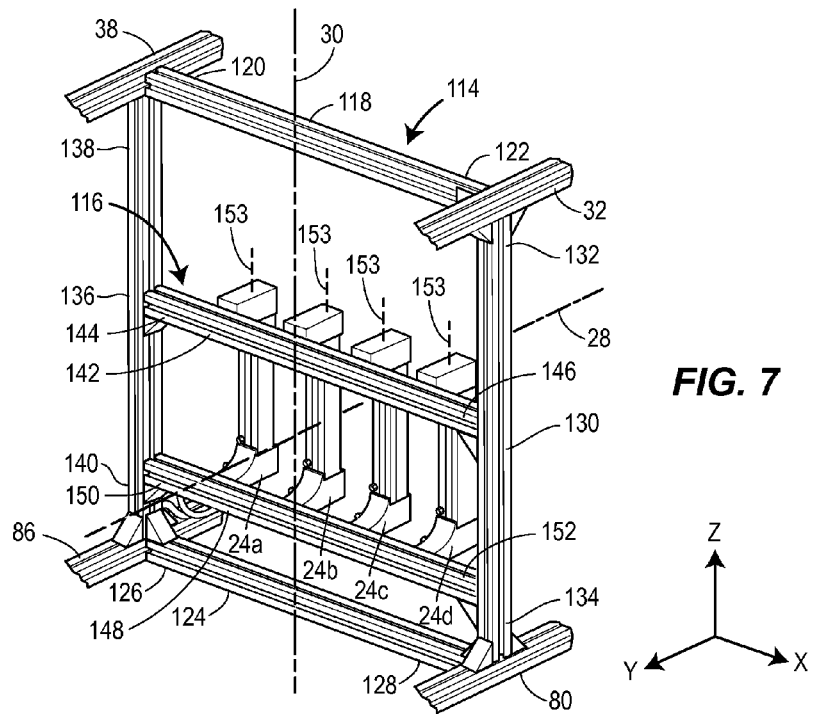
FIG. 7 is a perspective view of the heating support assembly of the embodiment of FIG. 1.

As illustrated in FIGS. 1 and 7, the primary assembly 114 may include any suitable number and configuration of frame members. For example, the primary assembly 114 may include a first primary member 118 that may be elongated and may have a longitudinal axis that extends in the second horizontal direction (i.e., parallel to or coaxial with the X-axis of the reference coordinate system provided in FIG. 1). The first primary member 118 may extend between the first upper frame member 32 and the second upper frame member 38. The first primary member 118 may have a first end 120 and a second end 122 that is longitudinally-opposite to the first end 120. The first end 120 of the first primary member 118 may be directly or indirectly secured to the second upper frame member 28 in any manner to allow the first primary member 118 to translate along or parallel to the first adjustment axis 28. For example, a feature of the first end 120 may be received into a longitudinal slot formed in the second upper frame member 28. Alternatively, the first end 120 of the first primary member 118 may be secured to a displaceable collar that surrounds all or part of the second upper frame member 28. In other embodiments, the first end 120 of the first primary member 118 may be secured to a vertical element of the primary assembly 114. In addition, the second end 122 of the first primary member 118 may be directly or indirectly secured to the first upper frame member 32 in any manner to allow the first primary member 118 to translate along or parallel to the first adjustment axis 28, such as by the examples provided above.

The primary assembly 114 may include a second primary member 124 that may be elongated and may have a longitudinal axis that extends in the second horizontal direction. The second primary member 124 may extend between the first lower frame member 80 and the second lower frame member 86. The second primary member 124 may have a first end 126 and a second end 128 that is longitudinally-opposite to the first end 126. The first end 126 of the second primary member 124 may be directly or indirectly secured to the second lower frame member 86 and the second end 128 of the second primary member 124 may be directly or indirectly secured to the first lower frame member 80 in any manner to allow the second primary member 124 to translate along or parallel to the first adjustment axis 28, such as by the examples provided above.

The primary assembly 114 may include a third primary member 130 that may be elongated and may have a longitudinal axis that extends in the vertical direction. The third primary member 130 may extend between the first upper frame member 32 and the first lower frame member 80. The third primary member 130 may have a first end 132 and a second end 134 that is longitudinally-opposite to the first end 132. The first end 132 of the third primary member 130 may be directly or indirectly secured to the first upper frame member 32 and the second end 134 of the third primary member 130 may be directly or indirectly secured to the first lower frame member 80 in any manner to allow the third primary member 130 to translate along or parallel to the first adjustment axis 28, such as by the examples provided above.

The primary assembly 114 may include a fourth primary member 136 that may be elongated and may have a longitudinal axis that extends in the vertical direction. The fourth primary member 136 may extend between the second upper frame member 38 and the second lower frame member 86. The fourth primary member 136 may have a first end 138 and a second end 140 that is longitudinally-opposite to the first end 138. The first end 138 of the fourth primary member 136 may be directly or indirectly secured to the second upper frame member 38 and the second end 140 of the fourth primary member 136 may be directly or indirectly secured to the second lower frame member 86 in any manner to allow the fourth primary member 136 to translate along or parallel to the first adjustment axis 28.

As illustrated in FIGS. 1 and 7, the secondary assembly 116 of the heating support assembly 22 may be carried by the primary assembly 114. The at least one heating element 24 may be secured to the secondary assembly 116 such that the secondary assembly 116 and the at least one heating element 24 translate in a vertical and/or horizontal direction relative to the primary assembly 114 and relative to the fixed target material 20. That is, the secondary assembly 116 may translate relative to the primary assembly 114 to displace the secondary assembly 116 along the second adjustment axis 30.

The secondary assembly 116 may include any suitable number or configuration of frame members. For example, the secondary assembly 116 may include a first secondary member 142 that may be elongated and may have a longitudinal axis that extends in the second horizontal direction. The first secondary member 142 may extend between the third primary member 130 and the fourth primary member 136. The first secondary member 142 may have a first end 144 and a second end 146 that is longitudinally-opposite to the first end 144. The first end 144 of the first secondary member 142 may be directly or indirectly secured to the fourth primary member 136 in any manner to allow the first secondary member 142 to translate along or parallel (or substantially along or substantially parallel) to the second adjustment axis 30, which may vertically extend on or along the second plane 26. For example, a feature of the first end 144 may be received into a longitudinal slot formed in the fourth primary member 136. Alternatively, the first end 144 of the first secondary member 142 may be secured to a displaceable, lockable collar that surrounds all or part of the fourth primary member 136. In addition, the second end 146 of the first secondary member 142 may be directly or indirectly secured to the third primary member 130 in any manner to allow the first secondary member 142 to translate along or parallel to the second adjustment axis 30, such as by the examples provided above.

As illustrated in FIGS. 1 and 7, the secondary assembly 116 may also include a second secondary member 148 that may be elongated and may have a longitudinal axis that extends in the second horizontal direction. The longitudinal axis of the second secondary member 148 may be vertically offset from the longitudinal axis of the first secondary member 142. The second secondary member 148 may extend between the third primary member 130 and the fourth primary member 136. The second secondary member 148 may have a first end 150 and a second end 152 that is longitudinally-opposite to the first end 150. The first end 150 of the second secondary member 148 may be directly or indirectly secured to the fourth primary member 136 and the second end 152 of the second secondary member 148 may be directly or indirectly secured to the third primary member 130 in any manner to allow the second secondary member 148 to translate along or parallel to the second adjustment axis 30, such as by the examples provided above.

The disclosed frame members of the primary and secondary assembly 114, 116 may have any suitable shape. For example, each frame member may include a tube with four longitudinal walls that are arranged to have a rectangular or square cross-sectional shape, and the four longitudinal walls may cooperate to define a hollow interior to reduce the weight of the frame members. The cross-sectional shape may be uniform along the entire longitudinal axis, or the cross-sectional shape may vary. A plurality of longitudinal ridges may be disposed on one of more of the four longitudinal walls to stiffen the frame members. The frame members may be made from any suitable material, such as a non-combustible material (e.g., aluminum or plastic).

As illustrated in FIGS. 1, 4, 5, and 7, the secondary assembly 116 of the heating support assembly 22 may also include one or more heating elements 24. Each heating element 24 may be elongated and may extend along a longitudinal axis 153 (see, FIG. 7). Each heating element 24 may be secured or fixed to each of the first secondary member 142 and the second secondary member 148 such that when the first secondary member 142 and the second secondary member 148 displace along or parallel to the second adjustment axis 30, each heating element 24 also displaces along or parallel to the second adjustment axis 30. The longitudinal axis 153 of the heating element 24 may be arranged or disposed in (or slightly offset from) the second plane 26. That is, the longitudinal axis 153 of each heating element 24 may be disposed along or adjacent to (or generally along or adjacent to) the second plane 26 such that when the heating support assembly 22 translates along the first adjustment axis 28, the second plane 26 also translates along the first adjustment axis 28. The second plane 26 may be parallel to the first plane 18 (i.e., parallel to or disposed in the X-Z plane of the reference coordinate system of FIG. 1) or may be disposed at an angle relative to the first plane 18.

Each heating element 24 may be fixed to each of the first secondary member 142 and the second secondary member 148. However, each heating element 24 may also be adjustable relative to each of the first secondary member 142 and the second secondary member 148. For example, each heating element 24 may be rotatable about its longitudinal axis 153, and/or each heating element 24 may be individually displaceable along the longitudinal axis of the first and second secondary members 142, 148 (i.e., normal to the second adjustment axis 30). Each heating element 24 may be a radiating heat element. Thus, the horizontal spacing and/or position of the heating elements 24 along the first and second secondary members 142, 148 can be adjusted. Thus, the heating elements 24 may transfer radiant energy to an object without physically contacting the object. The heating element 24 may include a heat source and a reflective surface that directs and concentrates the heat energy from the heat source, for example. The secondary assembly 116 may include any number of heating elements 24, such as a plurality of heating elements 24. For example, the secondary assembly 116 may include a first heating element 24a, a second heating element 24b, a third heating element 24c, and/or fourth heating element 24d equally or unequally spaced apart or adjacent to each other, for example.

Figure 8:
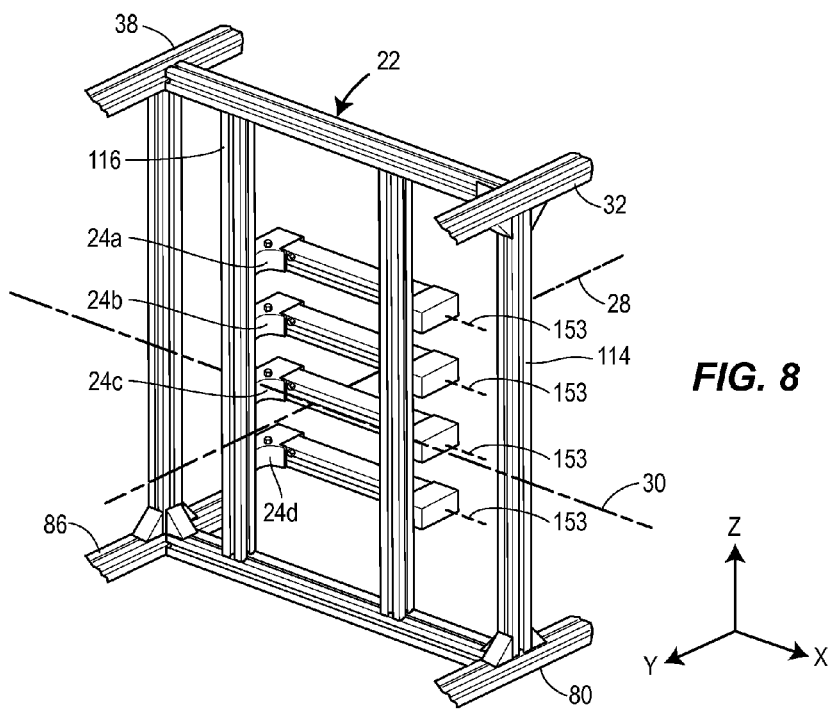
FIG. 8 is a perspective view of a heating support assembly of a second embodiment of a heat-generating apparatus.

In an alternative embodiment illustrated in FIG. 8, each of the first secondary member 142 and the second secondary member 148 of the secondary assembly 116 may be vertically disposed and may extend between the first primary member 118 and the second primary member 124. So configured, the secondary assembly 116 may displace along a second adjustment axis 30 that may be horizontal and that may be parallel to or coaxial with the X-axis of the reference coordinate system provided in FIG. 1 (i.e., in the second horizontal direction). Alternatively, the secondary assembly 116 may be secured to the primary assembly 114 such that the secondary assembly 116 displaces along a second adjustment axis 30 that is at an oblique angle with the Z-axis of the reference coordinate system provided in FIG. 1.

In alternative embodiments, one or more of the heating elements 24 may be disposed such that the corresponding longitudinal axis 153 is disposed at an oblique angle with the Z-axis of the reference coordinate system provided in FIG. 1. In addition, a first one of the one or more of the heating elements 24 may be disposed such that the corresponding longitudinal axis 153 is not parallel to the corresponding longitudinal axis 153 of a second one of the one or more of the heating elements 24. For example, the longitudinal axis 153 of the first one of the one or more of the heating elements 24 may be horizontal and the longitudinal axis 153 of the second one of the one or more of the heating elements 24 may be vertical.

The secondary assembly 116 and the primary assembly 114 of the heating support assembly 22 may be displaced in any suitable manner. Specifically, the primary assembly 114 may have a manual locking mechanism that allows the heating support assembly 22 to be manually translated and locked in a desired position. Similarly, the secondary assembly 116 may have a manual locking mechanism that allows the secondary assembly 116 to be manually translated and locked in a desired position. Alternatively, the secondary assembly 116 and/or the primary assembly 114 may be translated by a motor or other automated drive system (e.g., a mechanical drive) that may be directly or indirectly operatively coupled to the secondary assembly 116 and/or the primary assembly 114.

Figure 3:
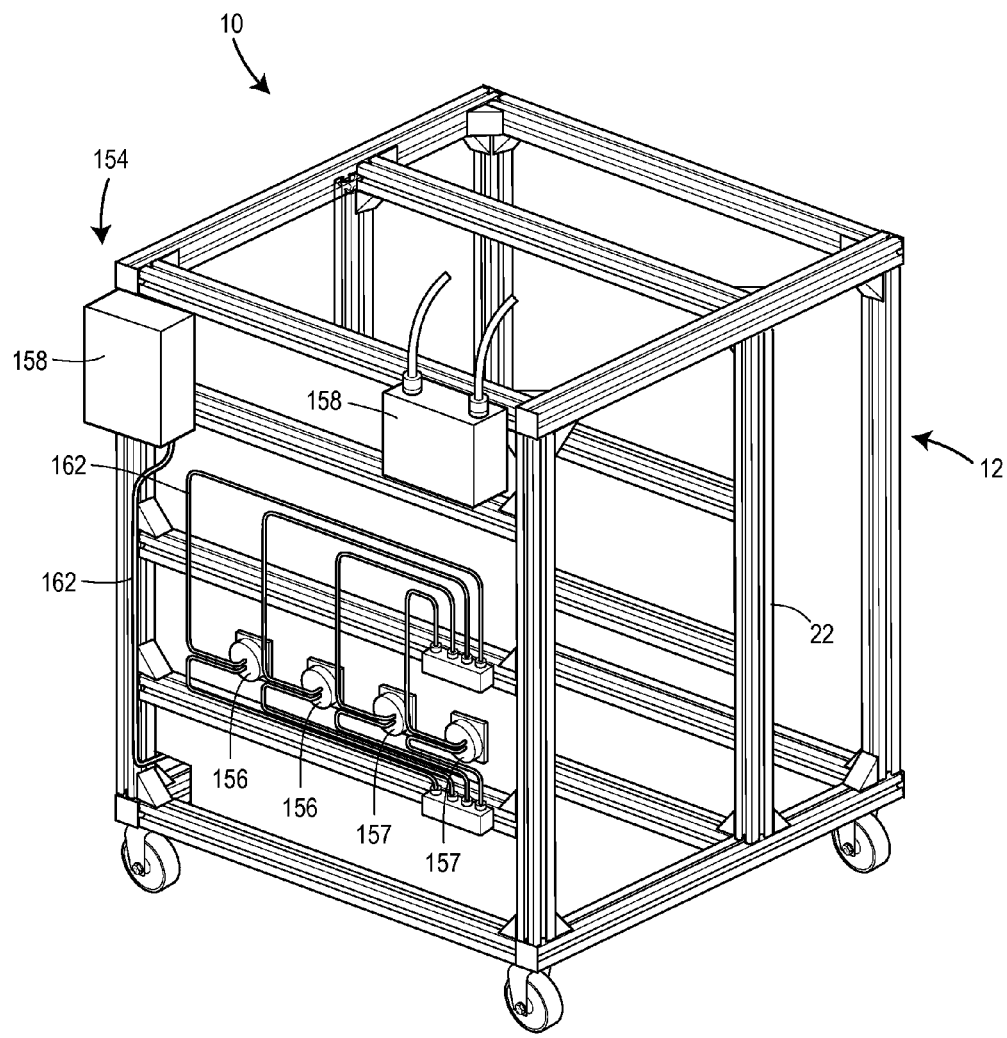
FIG. 3 is a second perspective view of the embodiment of FIG. 1.

As illustrated in FIGS. 3 and 4, the heat-generating apparatus 10 may also include a control system 154 that may include one or more heat flux gauges 156 and a controller 158. Each heat flux gauge 156 may correspond to a heating element 24 and may be communicatively coupled to the controller 158 and/or to the corresponding heating element 24 such that each of the heating elements 24 can be independently and separately calibrated to generate a target amount of heat. Each heat flux gauge 156 may be communicatively coupled to the controller 158 and/or to the corresponding heating element 24 by one or more communication lines 162 or by a wireless connection. Each heat flux gauge 156 may be secured to a portion of the securement assembly 14, such as a back surface of the panel member 16, and the heat flux gauge 156 may be adapted to detect the amount of heat flux (i.e., heat intensity) generated by the corresponding heating element 24 and/or the heat generated by the smoldering of the target material 20. The controller 154 may include a single enclosure or more than one enclosure, and the enclosure(s) may be secured to the securement assembly 14.

Instead of (or in addition to) the one or more heat flux gauges 156, one or more temperature measurement devices 157 (e.g., thermocouples, thermometers, etc.) may also be used. Each temperature measurement device 157 may correspond to a heating element 24 and may be communicatively coupled to the controller 158 and/or to the corresponding heating element 24 such that each of the heating elements 24 can be independently and separately calibrated to generate a target amount of heat (e.g., a target temperature). Each temperature measurement device 157 may be communicatively coupled to the controller 158 and/or to the corresponding heating element 24 by one or more communication lines 162 or by a wireless connection. Each temperature measurement device 157 may be secured to a portion of the securement assembly 14, such as a back surface of the panel member 16, and the temperature measurement device 157 may be adapted to detect the temperature generated by the corresponding heating element 24 and/or the temperature generated by the smoldering of the target material 20.

The controller 158 of the control system 154 may also be communicatively coupled to each of the heating elements 24 to precisely control the heat generated by each device independently. More specifically, a first command may be input into the controller 158 that is communicatively coupled to a first heating element 24a to regulate a temperature and/or a heat intensity of the first heating element 24a and a second command may be input into the controller 158 that is communicatively coupled to a second heating element 24*b* to regulate a temperature and/or a heat intensity of the second heating element 24*b*, and the first command may be independent or different than the second command to result in different resulting temperatures and/or heat intensity for each of the first heating element 24*a* and the second heating element 24*b*. Each of the heating elements 24 may be communicatively coupled to the controller 158 by one or more communication lines 162 or by a wireless connection. Power may also be provided to each of the heating elements 24 by a power line, and each power line may be coupled and regulated by to the controller 158. Alternatively, power may be provided to each of the heating elements 24 by a power line that is not coupled to the controller 158.

The control system 154 may also include a cooling assembly 160 (see FIG. 4) that is adapted to provide cooling fluid to each of the heating elements 24 during use. The cooling assembly 160 may be secured to any suitable portion of the frame assembly 12 or the heating support assembly 22, such as the secondary assembly 116. More particularly, the cooling assembly 160 may be secured to the second secondary member 148, and the cooling assembly 160 may be communicatively coupled to the controller 158 by one or more communication lines 162 or by a wireless connection.

The controller 158 may include one or more interfaces that allow a user to enter information or to receive information. For example, the controller 158 may include controls for a motor or mechanical drive, and the controller 158 may be operatively coupled to the motor or mechanical drive to position the primary assembly 114 at a desired position along the first adjustment axis 28 and/or to position the secondary assembly 116 at a desired position along the second adjustment axis 30. The position of each heating element 24 may also be controlled by an interface on the controller 158. The controller 158 may include a microprocessor and a memory and may include one or more communication interfaces 1001 (i.e., see FIG. 1, a USB interface, a serial plug interface, and/or a wireless interface) to allow the controller 128 to communicate with a remote user or remote computer 1000 (see FIG. 1). The controller 158 may have an input interface, such as a keypad or a touch screen, to allow information to be supplied to the controller 158. For example, a target temperature or a heating time may be input. As an additional example, each individual heating element 24 may be supplied with a corresponding target temperature that may change as a function of time. The memory may store a preset program that results in a set time or temperature for each heating element 24, and/or in a preset distance of the heating elements 24 from the target material 20.

To test a device (e.g., a smoke detector 164, as illustrated in FIG. 4) or expose a device to smoke using the heat-generating apparatus 10, the target material 20 is coupled or affixed to the securement assembly 14. The target material 20 may be any material that, when heated to a critical temperature, generates a desired amount of smoke and solid particulate. The target material 20 may include a wood material, a foam material, a cardboard material, or a plastic material, for example, and the target material 20 may be rectangular in shape. To couple the target material 20 to the securement assembly 14, the target material 20 is positioned against the panel member 16 and a bottom edge of the target material 20 may be disposed on the support member 104. The one or more mounting clips 112 may be positioned to engage a portion of the target material 20 adjacent to a vertical side edge thereof, and, optionally, the lower portion 108*a* of the engagement member 108 of the arm assembly 106 may be placed against the target material 20 to prevent the target material from falling away from the panel 16. So configured, a surface of the target material 20 (e.g., a rear surface) may be in or parallel to the first plane 18, and an opposite surface (e.g., a front surface) may face the heating elements 24. Alternatively, the target material 20 may be tilted against the panel member 16 such that the target material 20 is disposed at an angle relative to the panel member 16.

The smoke detector 164 (see FIG. 4) may be secured a desired distance above and offset from the securement assembly 14. That is, the smoke detector 164 having a vertical longitudinal axis may be secured in vertical alignment with an open top 200 (see FIG. 1) of the frame assembly 12 in an area which is to be heated. However, the vertical longitudinal axis of the smoke detector may be vertically and horizontally offset from the open top 200 of the frame assembly 12. For example, the heat-generating apparatus 10 could be used to generate a consistent smoke in a structure such as a house in order to evaluate responsiveness of local and remote smoke detectors 164. The heating support assembly 22 may then be moved into a desired position. More specifically, the primary assembly 114 of the heating support assembly 22 may be moved to a desired location along the first adjustment axis 28. The primary assembly 114 may be manually displaced or may be displaced by a mechanism controlled by the controller 158. The secondary assembly 116 of the heating support assembly 22 may also be moved to a desired location along the second adjustment axis 30. The secondary assembly 116 may be manually displaced or may be displaced by a mechanism controlled by the controller 158. Finally, each of the heating elements 24 may be adjusted by rotating each about its longitudinal axis 153 and/or displacing each normal to the second adjustment axis 30.

With the target material 20, the smoke detector 164, and the heating support assembly 22 in position, the one or more heating elements 24 may be engaged to remotely supply heat to the target material 20 to heat one or more portions of the target material 20 until smoldering occurs. As smoldering occurs, smoke and particulate matter from the target material is heated and naturally rises up through the open top 200 of the frame assembly. The smoke and particulate matter then impinges upon the smoke detector 164 and its associated sensors, etc. Through this process, the controller 158 of the heat generating apparatus 10 of a remote computer 1000, as shown in FIG. 1 for example, can be communicably coupled to the smoke detector 164 and monitor the performance and responses of the sensor(s) in the smoke detector. The data gathered throughout this test can be stored and analyzed to determine the quality of the performance of the smoke detector for example.

The disclosed heat-generating apparatus 10 controllably smolders a target material 20 without the heating component altering the generated smoke and gases. While this has been disclosed herein in relation to testing smoke detectors 164, the disclosed heat-generating apparatus 10 could be used to perform other tasks, including simply generating smoke.

In view of the foregoing, it should be appreciated that by varying the position of the heating support assembly 22 and/or the heat intensity of the individual heating elements 24, the incident heat flux generated by the one or more heating elements 24 may be easily measured via the heat flux gauges 156 and subsequently adjusted via the controller 158 to achieve desired smoldering of the target material 20, thereby prolonging the period of time over which smoke is created. In addition, the combination of the open-top configuration of the frame assembly 12, the vertically aligned orientation of the target material and heating elements, and/or the horizontally-offset arrangement of the heating elements 24 from the target material allows for an unobstructed vertical path of the smoke and solid particulate to naturally rise from the target material 20 to the smoke detector 164. Moreover, the heating elements 24 are not damaged by the rising smoke and solid particulate. Additionally, because the individual heating elements 24 are easily positioned, programmed, and/or controlled by the controller 158, a precise amount of heat can be generated in a highly repeatable manner in a targeted area to result in smoldering but not combustion of various different types of materials over a variety of different tests.

While various embodiments have been described above, this disclosure is not intended to be limited thereto. Variations can be made to the disclosed embodiments that are still within the scope of the appended claims.

What is claimed is:

1. A heat-generating apparatus, comprising:
a frame assembly;
a securement assembly arranged in a first plane for supporting a target material;
a heating support assembly adjustably coupled to the frame assembly and including at least one heating element for heating the target material when supported in the securement assembly, the at least one heating element arranged in a second plane that is offset from the first plane and being displaceable along a first adjustment axis that is perpendicular to the first plane and along a second adjustment axis that is disposed in the second plane,
wherein the heating support assembly includes a primary assembly and a secondary assembly that is carried by the primary assembly, wherein the at least one heating element is secured to the secondary assembly and the secondary assembly translates relative to the primary assembly to displace the secondary assembly along the second adjustment axis.

2. The heat-generating apparatus of claim 1, wherein the frame assembly defines an open top located above the securement assembly to facilitate an unobstructed path for smoke and particulate matter to escape when the target material is heated.

3. The heat-generating apparatus of claim 1, wherein a plurality of heating elements are secured to the secondary assembly, and a first one of the plurality of heating elements is displaceable relative to a second one of the plurality of heating elements.

4. The heat-generating apparatus of claim 1, wherein the frame assembly includes a first upper frame member and a second upper frame member that is offset from the first upper frame member in a direction normal to the first adjustment axis, wherein each of the first upper frame member and the second upper frame member extends parallel to and offset from the first adjustment axis, and wherein the heating support assembly is adjustably secured to a portion of the first upper frame member and a portion of the second upper frame member.

5. The heat-generating apparatus of claim 1, wherein the second adjustment axis is vertical and disposed normal to the first adjustment axis.

6. The heat-generating apparatus of claim 1, wherein the second adjustment axis is horizontal and disposed normal to the first adjustment axis.

7. The heat-generating apparatus of claim 1, wherein the first plane is vertical and the first adjustment axis is horizontal.

8. The heat-generating apparatus of claim 1, wherein the second plane is vertical.

9. The heat-generating apparatus of claim 1, wherein the securement assembly is attached to the frame assembly and includes a panel member arranged in the first plane for supporting a target material.

10. The heat-generating apparatus of claim 1, wherein the target material is supported such that the target material is parallel to the first plane.

11. The heat-generating apparatus of claim 1, wherein the first plane is disposed at or adjacent to a longitudinal first end portion of the frame assembly, and, wherein the heating support assembly is displaceable along the first adjustment axis from the longitudinal first end portion of the frame assembly to a longitudinal second end portion of the frame assembly.

12. The heat-generating apparatus of claim 1, wherein the second adjustment axis is vertical or horizontal and disposed normal to the first adjustment axis.

13. The heat-generating apparatus of claim 1, wherein the first plane is disposed at or adjacent to a longitudinal first end portion of the frame assembly.

14. The heat-generating apparatus of claim 13, wherein the heating support assembly is displaceable along the first adjustment axis from the longitudinal first end portion of the frame assembly to a longitudinal second end portion of the frame assembly.

15. The heat-generating apparatus of claim 1, further comprising a control system, the control system including a controller that is communicatively coupled to the at least one heating element.

16. The heat-generating apparatus of claim 15, wherein the control system includes at least one temperature measurement device or heat flux gauge that is communicatively coupled to the controller, the at least one temperature measurement device or heat flux gauge adapted to detect a temperature or a heat flux generated by the at least one heating element or by the target material.

17. The heat-generating apparatus of claim 15, wherein the controller is communicatively coupled to at least one mechanical drive that is operatively coupled to the heating support assembly to displace the at least one heating element along the horizontal first adjustment axis and/or the vertical second adjustment axis.

18. The heat-generating apparatus of claim 1, further comprising a control system, the control system including a controller that is communicatively coupled to the at least one heating element.

19. The heat-generating apparatus of claim 18, wherein the control system includes at least one temperature measurement device or heat flux gauge that is communicatively coupled to the controller, the at least one temperature measurement device or heat flux gauge adapted to detect a temperature or a heat flux generated by the at least one heating element or by the target material.

20. The heat-generating apparatus of claim 18, wherein the controller is communicatively coupled to at least one mechanical drive that is operatively coupled to the heating support assembly to displace the at least one heating element along the horizontal first adjustment axis and/or the vertical second adjustment axis.

21. A method of generating smoke, the method comprising:
positioning a target material on a securement assembly of a heat-generating apparatus;
adjusting a position of at least one heating element relative to the target material, the at least one heating element being spaced from the target material along a first adjustment axis and being carried by a heating support assembly that is movably coupled to a frame assembly that includes an open top at least above the securement assembly; and activating the at least one heating element to apply heat to the target material to smolder the target material and generate smoke, wherein adjusting a position of the heating support assembly includes adjusting a position of a primary assembly along the first adjustment axis and adjusting a position of the secondary assembly along a second adjustment axis, wherein the at least one heating element is secured to the secondary assembly.

22. The method of generating smoke of claim 21, wherein two or more heating elements are secured to the secondary assembly.

23. The method of generating smoke of claim 21, wherein the second adjustment axis is vertical and the first adjustment axis is horizontal.

24. The method of generating smoke of claim 21, wherein adjusting the position of the at least one heating element includes adjusting the vertical and/or horizontal position of the at least one heating element.

25. The method of generating smoke of claim 21, wherein the at least one heating element is oriented vertically.

26. The method of generating smoke of claim 21, wherein the target material is oriented vertically.

27. The method of generating smoke of claim 21, further comprising:
receiving a command with a controller that is communicatively coupled to the at least one heating element; and
regulating a temperature and/or a heat flux of the heating element based on the command.

28. The method of generating smoke of claim 21, further comprising:
receiving a first command with a controller that is communicatively coupled to a first heating element;
regulating a temperature and/or a heat flux of the first heating element based on the first command;
receiving a second command with the controller that is communicatively coupled to a second heating element; and
regulating a temperature and/or a heat flux of the second heating element based on the second command, wherein the first command is different than the second command.

29. The method of generating smoke of claim 21, further comprising:
detecting a temperature and/or a heat flux of the at least one heating element with a temperature measuring device and/or a heat flux gauge that is communicatively coupled to the controller.

30. The method of generating smoke of claim 29, further comprising:
automatically increasing or decreasing the temperature and/or the heat flux of the at least one heating element based on the detected temperature or heat flux.

31. A method of testing a device, the method comprising:
positioning a target material on a securement assembly of a heat-generating apparatus, the securement assembly supported on a frame assembly that defines an open top at a location above the securement assembly;
positioning the device at a location above the open top of the frame assembly;
activating at least one heating element to apply heat to the target material to smolder the target material and generate smoke that can escape through the open top, the at least one heating element being spaced from the target material along a first adjustment axis;
gathering data representative of performance of the device with a controller communicably coupled to the device; and
adjusting a position of the at least one heating element relative to the target material prior to activating the at least one heating element,
wherein adjusting the position of a heating support assembly includes adjusting a position of a primary assembly along the first adjustment axis and adjusting a position of the secondary assembly along a second adjustment axis, wherein the at least one heating element is secured to the secondary assembly.

32. The method of testing a device of claim 31, wherein the first adjustment axis is horizontal and the second adjustment axis is vertical and disposed normal to the first adjustment axis.

33. The method of testing a device of claim 31, further comprising:
receiving a command with a controller that is communicatively coupled to the at least one heating element; and
regulating a temperature or heat flux of the heating element based on the command.

34. The method of testing a device of 31, further comprising:
receiving a first command with a controller that is communicatively coupled to a first heating element;
regulating a temperature and/or a heat flux of the first heating element based on the first command;
receiving a second command with the controller that is communicatively coupled to a second heating element; and
regulating a temperature and/or a heat flux of the second heating element based on the second command, wherein the first command is different than the second command.

35. The method of testing a device of claim 31, wherein the device is a smoke alarm.

36. The method of testing a device of claim 31, further comprising:
detecting a temperature and/or a heat flux of the at least one heating element with a temperature measuring device and/or a heat flux gauge that is communicatively coupled to the controller.

37. The method of testing a device of claim 36, further comprising:
automatically increasing or decreasing the temperature and/or the heat flux of the at least one heating element based on the detected temperature and/or heat flux.

38. A heat-generating apparatus, comprising:
a frame assembly;
a securement assembly arranged in a first plane for supporting a target material;
a heating support assembly adjustably coupled to the frame assembly and including at least one heating element for heating the target material when supported in the securement assembly, the at least one heating element arranged in a second plane that is offset from the first plane and being displaceable along a first adjustment axis that is perpendicular to the first plane and along a second adjustment axis that is disposed in the second plane,
wherein the frame assembly includes a first upper frame member and a second upper frame member that is offset from the first upper frame member in a direction normal to the first adjustment axis, wherein each of the first upper frame member and the second upper frame member extends parallel to and offset from the first adjustment axis, and wherein the heating support assembly is adjustably secured to a portion of the first upper frame member and a portion of the second upper frame member.

39. The heat-generating apparatus of claim 38, wherein the frame assembly defines an open top located above the securement assembly to facilitate an unobstructed path for smoke and particulate matter to escape when the target material is heated.

40. The heat-generating apparatus of claim 38, wherein the heating support assembly includes a primary assembly and a secondary assembly that is carried by the primary assembly, wherein the at least one heating element is secured to the secondary assembly and the secondary assembly translates relative to the primary assembly to displace the secondary assembly along the second adjustment axis, and wherein a plurality of heating elements are secured to the secondary assembly, and a first one of the plurality of heating elements is displaceable relative to a second one of the plurality of heating elements.

41. The heat-generating apparatus of claim 38, wherein the first plane is vertical and the first adjustment axis is horizontal.

42. The heat-generating apparatus of claim 38, wherein the second plane is vertical.

43. The heat-generating apparatus of claim 38, wherein the securement assembly is attached to the frame assembly and includes a panel member arranged in the first plane for supporting a target material.

44. The heat-generating apparatus of claim 38, wherein the target material is supported such that the target material is parallel to the first plane.

* * * * *

UNITED STATES PATENT AND TRADEMARK OFFICE
CERTIFICATE OF CORRECTION

PATENT NO. : 9,247,584 B2
APPLICATION NO. : 13/837260
DATED : January 26, 2016
INVENTOR(S) : Zoltan Thomas Fabian et al.

It is certified that error appears in the above-identified patent and that said Letters Patent is hereby corrected as shown below:

In the Claims:

At Column 16, line 24, claim 34, "31," should be -- claim 31, --.

Signed and Sealed this
Twelfth Day of July, 2016

Michelle K. Lee
*Director of the United States Patent and Trademark Office*